(12) United States Patent
Burgos et al.

(10) Patent No.: US 7,884,243 B2
(45) Date of Patent: Feb. 8, 2011

(54) PROCESS FOR THE SYNTHESIS OF ENEAMIDE DERIVATIVES

(75) Inventors: Alain Burgos, Les Ponts-De-Ce (FR); Blandine Bertrand, Angrie (FR); Sonia Roussiasse, Champigne (FR); Jean-François Pluvie, Angers (FR); Sylvie Blanchet, Feneu (FR); Juliette Martin, Angers (FR); Florence Perrin, Avrille (FR); Françoise Bourdeau, Montreuil-Juigne (FR)

(73) Assignee: Zach System, Avrille (FR)

( * ) Notice: Subject to any disclaimer, the term of this patent is extended or adjusted under 35 U.S.C. 154(b) by 0 days.

(21) Appl. No.: 10/583,902

(22) PCT Filed: Dec. 22, 2004

(86) PCT No.: PCT/IB2004/004363

§ 371 (c)(1),
(2), (4) Date: Jun. 21, 2006

(87) PCT Pub. No.: WO2005/063687

PCT Pub. Date: Jul. 14, 2005

(65) Prior Publication Data
US 2007/0129573 A1  Jun. 7, 2007

(30) Foreign Application Priority Data
Dec. 22, 2003 (EP) ................... 03293281

(51) Int. Cl.
C07C 233/00 (2006.01)
(52) U.S. Cl. ........................ 564/123; 564/133
(58) Field of Classification Search ............... 564/123, 564/133
See application file for complete search history.

(56) References Cited

U.S. PATENT DOCUMENTS 3,375,287 A * 3/1968 Tinsley et. al. .............. 585/377
4,194,050 A   3/1980 Hazama

FOREIGN PATENT DOCUMENTS
WO   99/18065   4/1999

OTHER PUBLICATIONS

Burk et al. "A Three-Step Procedure for Asymmetric Catalytic Reductive Amidation of Ketones" Journal of Organic Chemistry (1998) 63 p. 6084-6085.

Li et al. "Synthesis of Chiral Hydroxyl Phospholanes from D-mannitol and Their Use in Asymmetric Catalytic Reactions" Journal of Organic Chemistry (2000) 65 p. 3489-3496.

Zhang et al. "Highly Enantioselective Hydrogenation of Cyclic Enamides Catalyzed by a Rh-PennPhos Catalyst" Journal of Organic Chemistry (1999) 64 p. 1774-1775.

* cited by examiner

Primary Examiner—Sudhakar Katakam
(74) Attorney, Agent, or Firm—Merchant & Gould PC

(57) ABSTRACT

A process for the production of ene-amide derivatives represented by the formula (I)

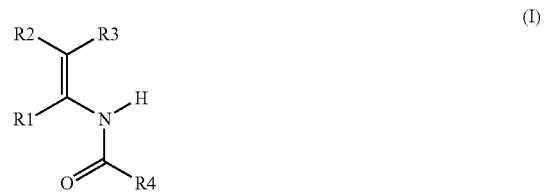

wherein R1 and R2 and R3 are independently a hydrogen atom, an alkyl, a cycloalkyl, a cycloalkylalkyl, an alkylaryl, an aryl, a heterocycle, a cyano, an alkoxy, an aryloxy, a carboxyl, a carbamoyl, —CONR5R6 (in which R5 and R6 are independently an alkyl, arylalkyl or aryl group said ring being substituted or not with a functional group or with R5) or —COOR5 group (in which R5 is an alkyl, alkylaryl or aryl group), said alkyl, cycloalkyl, cycloalkylalkyl, alkylaryl and aryl groups being substituted or not with a functional group or with R5; or R1 and R2 taken together, may form a ring (which terms includes mono-, di- and higher polycyclic ring systems); R4 is a hydrogen atom, an alkyl, an aryl, an alkylaryl, said groups are substituted or not with a halogen atom as Cl, Br, or F; X is an oxygen atom or a leaving group and m is an integer 1 or 2; when m is 1 then X is a leaving group; when m is 2 then X is a oxygen atom, which comprise: a hydrogenation/isomerization reaction in presence of a heterogeneous catalyst, of an oxime derivatives of formula (II)

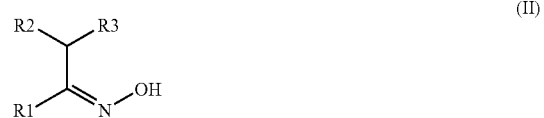

wherein R1, R2 and R3 are as defined above with an acyl derivative of formula (III) (R4CO)$_m$X wherein R4, m and X are as defined above.

15 Claims, No Drawings

PROCESS FOR THE SYNTHESIS OF ENEAMIDE DERIVATIVES

BACKGROUND OF THE INVENTION

The present invention relates to a new process for the large-scale preparation of ene-amide derivatives useful as valuable substrates for asymmetric hydrogenation reaction and hence for the synthesis of enantiomerically pure amines derivatives known as key intermediates for active pharmaceuticals.

Several methods have been described in the prior art, for example in WO 99/18065 to prepare ene-amide precursors, but these methods are clearly not very general and unsuitable for large-scale production.

The articles JOC, 1998, 63, p 6084 of the authors M. Burk and Coll. and JOC, 1999, 64(6), p 1775 of the authors X. Zhang and Coll. describe a process for ene-amide compounds synthesis comprising the reduction of oxime derivatives with iron metal in presence of acetic anhydride/acetic acid or acetic anhydride only.

The U.S. Pat. No. 4,194,050 patent describes a process for ene-amide compounds synthesis comprising the reduction of oxime derivatives with ruthenium catalyst in presence of carboxylic anhydride.

However, these processes show some limitations such as product decomposition under these conditions, use of co-solvent to facilitate product isolation, impure ene-amides which required arduous purifications and low to moderate yields.

Prior art processes are unsuitable for large-scale production of ene-amide derivatives and hence not applicable to the commercial preparation of chiral amines via asymmetric hydrogenation.

SUMMARY OF THE INVENTION

The process according to the invention presents the advantages of obtaining ene-amides in good yields, great facility of product isolation, an excellent chemical purity of product and reproducible process.

The process according to the present invention is clearly suitable for the large-scale industrial production of amine derivatives, via an asymmetric or not hydrogenation reaction. These amine derivatives, asymmetric or not, are used as intermediates for active pharmaceuticals preparation.

DETAILED DESCRIPTION

The present invention relates to a new process for the preparation of compounds of formula (I), comprising a hydrogenation-isomerization reaction of compound of formula (II) with an acyl derivative of formula (III) in presence of a heterogeneous catalyst as shown in scheme (I).

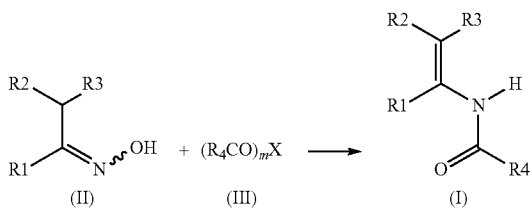

wherein

R1 and R2 and R3 are independently a hydrogen atom, an alkyl, a cycloalkyl, a cycloalkylalkyl, an alkylaryl, an aryl, a heterocycle, a cyano, an alkoxy, an aryloxy, a carboxyl, a carbamoyl, —CONR5R6 (in which R5 and R6 are independently an alkyl, arylalkyl, aryl group or R5 and R6 taken together may form a ring) or —COOR5 group (in which R5 is an alkyl, cycloalkyl, alkylaryl or aryl group), said alkyl, cycloalkyl, cycloalkylalkyl, alkylaryl and aryl groups being substituted or not with a functional group or with R5;

or R1 and R2 taken together, may form a ring (which terms includes mono-, di- and higher polycyclic ring systems), said ring being substituted or not with a functional group or with R5;

R4 is a hydrogen atom, an alkyl, an aryl, an alkylaryl, said groups are substituted or not with a halogen atom as Cl, Br, or F;

X is an oxygen atom or a leaving group and m is an integer 1 or 2;

when m is 1 then X is a leaving group; when m is 2 then X is a oxygen atom.

As used herein, unless the context otherwise requires:

The term "alkyl" preferably means a straight or branched alkyl group having 1 to 20 carbons atoms such as, but not limited to, methyl, ethyl, n-propyl, isopropyl, n-butyl, iso-butyl, sec-butyl, tert-butyl optionally substituted with a functional group or with R5.

The term "cycloalkyl" preferably means a cycloalkyl group having 3 to 20 carbon atoms, such as, but not limited to, cyclopropyl, cyclopentyl, cyclohexyl optionally substituted with a functional group or with R5.

The term "cycloalkylalkyl" preferably means a cycloalkylalkyl group having 3-20 carbon atoms such as but not limited to cyclopropylmethyl, cyclohexylmethyl optionally substituted with a functional group or with R5.

The term "aryl" preferably means an aryl group having 6 to 20 carbon atoms such as but not limited to phenyl, tolyl, xylyl, cumenyl, naphthyl optionally substituted with a functional group or with an alkyl or with a fused aryl, or "aryl" means a heteroaryl group having 6 to 20 carbon atoms comprising one or more heteroatom as O, N or S such as, but not limited to, furyl, thienyl, pyrrolyl, imidazolyl, pyridyl, pyrazyl, pyrimidinyl, indolyl, carbazolyl, isoxazolyl, isothiazolyl optionally substituted with a functional group or with R5 or with an alkyl or with a fused aryl.

The term "alkylaryl" preferably means an alkylaryl group having 6 to 20 carbon atoms such as, but not limited to, benzyl, phenethyl, naphthylmethyl optionally substituted with a functional group or with R5.

The term "heterocycle" preferably means a heterocycle group having 6 to 20 carbon atoms comprising one more heteroatom as O, N or S such as but not limited pyrrolidinyl, piperazinyl, piperidyl, imidazolidinyl, piperidyl, indolinyl, said heterocycle being saturated or not, said heterocycle being optionally substituted with a functional group or with R5 or a fused aryl group.

The term "functional group" means halogen atom, or a group comprising —OH, —OR5, —CN, —COOR5, —COR5, —CONR5R6, —OCOR5, —NH2, —NHR5, —NR5R6, —NO2, —SH, SR5, wherein R5 and R6 are independently an alkyl, an alkylaryl or an aryl group or R5 and R6 taken together may form a ring, The term "leaving group" means preferably one of the groups —COR5, —CO2R5, —SO2R5, —COCCl3, —SO2F, —SO2CF3, —SO2CH2CF3, wherein R5 is an alkyl, an alkylaryl or an aryl group The term "ring" preferably means the formation of ring having 4 to 30 carbon atoms, such as but not limited, compounds of formula hereunder

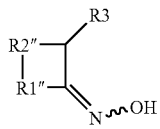

wherein —R1-R2- is a methylene, dimethylene, trimethylene, tetramethylene, pentamethylene or hexamethylene linkage optionally substituted with a functional group or a fused aryl.

The present invention is also relates to the most preferable compounds represented by the following formula:

formula (IIA)

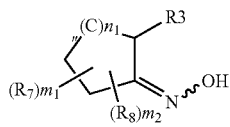

wherein n1 is an integer from 0 to 4, $m_1$ and $m_2$ are each an integer from 0 to 4, R7 and R8 different or same, are an hydrogen atom, a functional group, an alkyl, an aryl, a cycloalkyl, an alkylaryl.

formula (IIB)

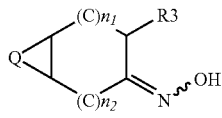

wherein each n1 and n2 is an integer from 0 to 4, Q is an aryl, heteroaryl, cycloaklyl, heterocycloalkyl said group are substituted or not with at least one functional group preferably alpha- or beta-tretralone-oxime derivatives, alpha- or beta-indanone-oxime derivatives, substituted or not with a functional group.

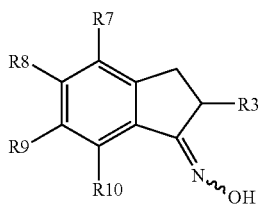

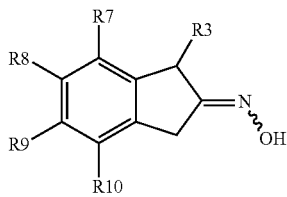

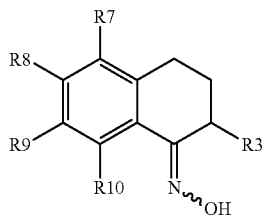

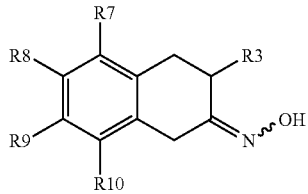

Wherein R3, R7, R8 are as defined above, R9, R10 are independently an hydrogen atom, a functional group, an alkyl, an aryl, a cycloalkyl, an alkylaryl.

Formula (IIC)

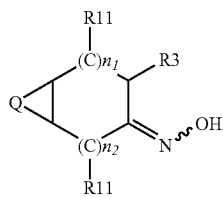

wherein n1, n2, R3 and Q are as defined above, R11 is a hydrogen atom, an alkyl, an aryl.

Formula (IID)

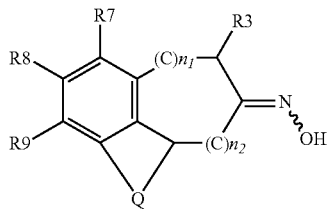

wherein n1, n2, R3, R7, R8, R9 and Q are as defined above.

Formula (IIE)

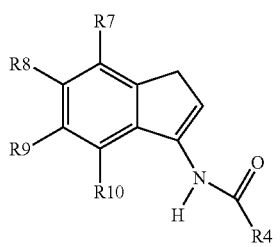

wherein

R4 is a hydrogen atom, an alkyl, an aryl, an alkylaryl, said groups are substituted or not with a halogen atom as Cl, Br, or F;

R7, R8, R9 and R10, identical or different, with not simultaneously an hydrogen atom, are an hydrogen atom, a functional group, an alkyl, an aryl, preferably R7, R8 and R10 are an hydrogen atom, R9 is a methoxy and R4 is a methyl.

The present invention relates also to the use of these most preferable compounds in an hydrogenation reaction, asymmetric or not, giving an amine or amide derivative for pharmaceutical interest.

Heterogeneous catalysts are based on metal like Pd, Ir, Pt, Rh, Ni catalysts preferably Ir or Rh.

The heterogeneous catalysts is used in the form of an oxide or metallic and may be supported on a suitable carrier (for example Ir/carbon, Ir/alumina, Rh/carbon or Rh/alumina).

The method how to carry out the present invention will be explained hereinafter.

The compound of formula (II) may be used as a syn-form, anti-form or a mixed-form of both.

The compound of formula (III) should be used in an amount of at least 2 molar equivalents for one molar equivalent of the oxime and may be used in a large amount as a reacting agent combined with a solvent.

The amount of the catalyst used is in the range of 0.001 to 30% mol, for 1 mol of the oxime derivative.

The process of the present invention is carried out in a suitable solvent. Suitable solvents are aprotic non-basic solvents such as ethers (such as but not limited tetrahydrofuran, tetrahydropyran, diethyl ether, etc.) or aromatic hydrocarbons (such as but not limited to benzene, toluene, etc.) or carboxylic anhydrides or halogenated hydrocarbons or lower carboxylic acids or mixtures thereof.

The process of the present invention is carried out under a temperature range of −20 to 150° C., preferably between 20° C. to 120° C.

The hydrogenation of the present invention is carried out under a hydrogen pressure between 0.5 to 20 bars.

The process of the present invention is carried out for a period of time in the range of 0.5 to 24 hours.

The process of the present invention can comprises a work up step of the organic solution of the compound of formula (I) which is a washing step with water containing organic or mineral salts without halogen atom, preferably without chloride.

These organic or mineral salts can be selected among phosphate, sulfate, acetate, citrate, formate, borate, carbonate, ammonium, preferably phosphate.

The washing step allows to obtain a solution with a neutral pH. The isolated product is halogen ions free. These halogen ions can interfere with the catalyst during the subsequent asymmetric hydrogenation reaction and thus can affect the yield of this reaction. As a result, this washing step allows to obtain a starting material of better quality for the next asymmetric hydrogenation reaction.

The invention will be better understood from the experimental details, which follow.

EXAMPLES

The present invention will be illustrated by the following examples, which will not limit the scope of the invention in any way.

Example 1

Enamide from β-tétralone

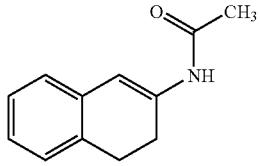

Example 1a

Enamide from β-tétralone with Rh/C

Into a 100 ml reactor are introduced tetrahydrofuran (43.5 ml) and 3,4-dihydo-1H-naphtalen-2-one oxime (7.2 g, 0.0447 mole). Then acetic anhydride (13.7 g, 0.134 mole) is added at 20-25° C. over a period of 15 minutes. The suspension is stirred for 1 hour and the catalyst 5% Rh/C (dry catalyst) (0.29 g, 4% by weight relative to oxime) is added. The mixture is heated to 30° C. and the hydrogen flow is started. Hydrogenation is continued over a period of 15 hours under 4 bars hydrogen pressure. After the end of the reaction, the suspension is filtered from the catalyst and the catalyst is washed with THF. This solution is added on a mixture of water (21 ml) and NaOH 30% (30.4 g) at 5° C. over a period of 1 hour and maintained at 20° C. during 30 minutes. The aqueous phase is discarded and the organic layer is washed with water saturated with NaCl.

THF is distilled under reduced pressure, replaced by toluene and concentrated under vacuum to give an oily brown residue of N-(3,4-Dihydro-naphthalen-2-yl)-acetamide (6.14 g, 74%).

Example 1b

Enamide from β-tétralone with Ir/C

Into a 100 ml reactor are introduced tetrahydrofuran (43.5 ml) and 3,4-dihydo-1H-naphtalen-2-one oxime (7.2 g, 0.047 mole). Then acetic anhydride (13.5 g, 0.134 mole) is added at 20-25° C. over a period of 15 minutes. The suspension is stirred for 1 hour and the catalyst 5% Ir/C (dry catalyst) (0.29 g, 4% by weight relative to oxime) is added. The mixture is heated to 70° C. and the hydrogen flow is started. Hydrogenation is continued over a period of 8 to 10 hours under 4 bars hydrogen pressure. After the end of the reaction, the suspension is filtered from the catalyst and the catalyst is washed with THF. This solution is added on a mixture of water (30 ml) and NaOH 30% (42 g) at 5° C. over a period of 1 hour and maintained at 20° C. during 30 minutes. The aqueous phase is discarded and the organic layer is washed with water saturated with NaCl.

THF is distilled under pressure, replaced by toluene and concentrated under vacuum to give an oily brown residue of N-(3,4-Dihydro-naphthalen-2-yl)-acetamide (5.5 g, 66%).

Example 1c

Enamide from β-tétralone with Ir/C 5.5 g (0.0341 mol) of 3,4-dihydro-1H-naphtalene-2-one oxime was dissolved in 42 ml of THF. Then 9.66 ml of acetic anhydride was added dropwise. The reaction mixture is stirred at a temperature between 20-30° C. during 2 hours. To this reaction mixture is added 0.44 g of the 5% Ir-carbon catalyts. Then the hydrogenation is carried out at a hydrogen pressure of 6 bars and at 75° C. during 3 hours. After the catalyst was filtered off, the filtrate was concentrated to dryness under reduced pressure. The residue was dissolved in 120 ml of toluene and concentrated to dryness under reduced pressure. This new residue was recrystallized in a mixture of 10 ml of MTBE and 9 ml of hexane to obtain 3.82 g of the product, the compound N-(3,4-dihydro-naphtalene-2-yl)acetamide.

Crude yield: quantitative/Isolated yield: 59.9-%
Chemical purity (GC): 98.95%.

Structural Analysis

Oxime: 1H NMR (CDCl3): 2.7-2.8 (t, 1H), 2.85-2.95 (t, 1H), 3-3.1 (m, 2H), 3.75 (s, 1H), 4.05 (s, 1H), 7.25-7.5 (m, 4H), 9.5 (m, OH).

Oxime acétate: 1H NMR (CDCl3): 2.2 (s, 3H), 2.65-2.9 (m, 4H), 3.65 (s, 1H), 3.85 (s, 1H), 7.1-7.25 (m, 4H).

Enamide: * 1H NMR (CDCl3): 2.3 (s, 3H), 2.6-2.75 (t, 2H), 3-3.15 (t, 2H), 7.15-7.35 (m, 5H), 7.75 (m, NH).

* 13C NMR (CDCl3): 168, 134, 133, 132.5, 127, 126, 125.5, 125, 27.5, 27, 24.

Example 2

Enamide from 6-methoxy-1-indanone

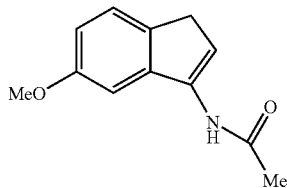

Example 2a

Enamide from 6-methoxy-1-indanone with Ir/C

The reaction is carried out in the same manner as in example 1b, except that 1-indanone-oxime, methoxy-6- is used as starting material. The yield is 83.8%.

The chemical purity is 98.4%.

Example 2b

Enamide from 6-methoxy-1-indanone with Ir/C

Into a 100 ml reactor are introduced tetrahydrofuran (24 ml) and 6-Methoxy-1-indanone oxime (4.5 g, 0.0254 mole). Then acetic anhydride (7.78 g, 0.0762 mole) is added at 20-25° C. over a period of 15 minutes. The suspension is stirred for 1 hour and the catalyst 5% Ir/C (dry catalyst)(0.225 g, 4% by weight relative to oxime) is added. The mixture is heated to 70-75° C. and the hydrogen flow is started. Hydrogenation is continued over a period of 1 to 2 hours under 4 bars hydrogen pressure. After the end of the reaction, the suspension is filtered from the catalyst and the catalyst is washed with THF. This solution is added on a mixture of water (15 ml) and NaOH 30% (13 ml) at 5° C. over a period of 1 hour and maintained at 20° C. during 30 minutes. The aqueous phase is discarded and the organic layer is washed with water saturated with NaCl.

The organic layer is concentrated under vacuum at 50° C. to give brown crystals of N-(6-Methoxy-3H-inden-1-yl)-acetamide (3.34 g, 70%).

Example 2c

Enamide from 6-methoxy-1-indanone with Rh/C

Into a 100 ml reactor are introduced tetrahydrofuran (24 ml) and 6-Methoxy-1-indanone oxime (4.5 g, 0.0254 mole). Then acetic anhydride (7.78 gr, 0.0762 mole) is added at 20-25° C. over a period of 15 minutes. The suspension is stirred for 1 hour and the catalyst 5% Rh/C (dry catalyst) (0.225 g, 4% by weight relative to oxime) is added. The mixture is heated to 30-35° C. and the hydrogen flow is started. Hydrogenation is continued over a period of 7 to 8 hours under 4 bars hydrogen pressure. After the end of the reaction, the suspension is filtered from the catalyst and the catalyst is washed with THF. This solution is added on a mixture of water (15 ml) and NaOH 30% (13 ml) at 5° C. over a period of 1 hour and maintained at 20° C. during 30 minutes. The aqueous phase is discarded and the organic layer is washed with water saturated with NaCl.

The organic layer is concentrated under vacuum at 50° C. to give off-white crystals of N-(6-Methoxy-3H-inden-1-yl)-acetamide (3.82 g, 80%).

Example 2d

Enamide from 6-methoxy-1-indanone with Rh/C

Into a 250 ml reactor are introduced tetrahydrofuran (50 ml) and 1-indanone-oxime, methoxy-6-(10 g, 0.056 mole). Then acetic anhydride (17.3 g, 0.170 mole) is added at 20-25° C. over a period of 15 minutes. The suspension is stirred for 1 hour and the catalyst 5% Rh/C (dry catalyst) (0.40 g, 4% by weight relative to oxime) is added, rinsed by tetrahydrofuran (10 ml). The mixture is heated to 30° C. and the hydrogen flow is started. Hydrogenation is continued over a period of 15 hours under 4 bars hydrogen pressure. After the end of the reaction, the suspension is filtered from the catalyst and the catalyst is washed with THF. This solution is added on a mixture of water (29 ml) and NaOH 30% (42.2 g) at 5° C. over a period of 1 hour and maintained at 20° C. during 30 minutes. The aqueous phase is discarded and the organic layer is washed with a buffer solution of sodium dihydrogen phosphate (37.8 w/w) adjusted at pH 6 with NaOH 30%.

THF is distilled under reduced pressure, replaced by toluene and concentrated under vacuum to give an oily brown residue of N-(6-Methoxy-3H-inden-1-yl)-acetamide (6.6 g, 57.5%)

Structural Analysis

Oxime: * 1H NMR 270 MHz JEOL (DMSO): 2.7-2.95 (m, 4H), 3.75 (s, 3H), 6.9 (m, 1H), 7 (m, 1H), 7.25 (d, 1H), 10.8 (s, OH).

* 13C NMR (DMSO): δ 165, 162, 150, 147, 137, 127, 112, 67, 34, 32.

Oxime acetate: * 1H NMR (CDCl3): 2.15 (s, 3H), 2.95 (m, 4H), 3.7 (s, 3H), 6.85-6.95 (m, 1H), 7.1-7.15 (m, 1H), 7.25 (m, 1H).

* 13C NMR (CDCl3): 171, 168, 158, 143, 135, 126, 122, 105, 56, 29, 28, 19.

Enamide: * 1H NMR (CDCl3): 3 (s, 3H), 3.6 (s, 3H), 4.1 (d, 2H), 7.5-7.6 (dd, 1H), 7.65 (m, 2H), 8.05-8.15 (d, 1H), 8.45 (s, 1H).

* 13C NMR (CDCl3): 169, 158, 140, 136, 134, 123, 117, 110, 103, 55, 35, 23.

Example 3

Enamide from α-tétralone

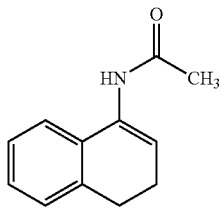

Example 3a

Enamide from α-tétralone with Rh/C

Into a 180 ml reactor are introduced tetrahydrofuran (60 ml) and 3,4-dihydo-2H-naphtalen-1-one oxime (10 g, 0.062 mole). Then acetic anhydride (19 g, 0.186 mole) is added at 20-25° C. over a period of 15 minutes. The suspension is stirred for 1 hour and the catalyst 5% Rh/C (dry catalyst) (0.4 g, 4% by weight relative to oxime) is added. The mixture is heated to 30° C. and the hydrogen flow is started. Hydrogenation is continued over a period of 15 to 20 hours under 4 bars hydrogen pressure. After the end of the reaction, the suspension is filtered from the catalyst and the catalyst is washed with THF. This solution is added on a mixture of water (30 ml) and NaOH 30% (42 g) at 5° C. over a period of 1 hour and maintained at 20° C. during 30 minutes. The aqueous phase is discarded and the organic layer is washed with water saturated with NaCl.

THF is distilled under reduced pressure and replaced by toluene; the suspension is stirred at 5° C. for 1 hour then the precipitate is filtered off and washed twice with 10 ml of cold toluene.

Crystals are dried under vacuum at 50° C. to give N(3,4-dihydro-1-naphtalenyl)Acetamide (9.74 g, 84%).

Example 3b

Enamide from α-tétralone with Ir/C

Into a 180 ml reactor are introduced tetrahydrofuran (60 ml) and 3,4-dihydo-2H-naphtalen-1-one oxime (10 g, 0.062 mole). Then acetic anhydride (19 g, 0.186 mole) is added at 20-25° C. over a period of 15 minutes. The suspension is stirred for 1 hour and the catalyst 5% Ir/C (dry catalyst) (0.4 g, 4% by weight relative to oxime) is added. The mixture is heated to 70° C. and the hydrogen flow is started. Hydrogenation is continued over a period of 4 to 5 hours under 4 bars hydrogen pressure. After the end of the reaction, the suspension is filtered from the catalyst and the catalyst is washed with THF. This solution is added on a mixture of water (30 ml) and NaOH 30% (42 g) at 5° C. over a period of 1 hour and maintained at 20° C. during 30 minutes. The aqueous phase is discarded and the organic layer is washed with water saturated with NaCl.

THF is distilled under reduced pressure and replaced by toluene; the suspension is stirred at 5° C. for 1 hour then the precipitate is filtered off and washed twice with 10 ml of cold toluene.

Crystals are dried under vacuum at 50° C. to give N(3,4-dihydro-1-naphtalenyl) Acetamide (9.18 g, 79%).

Structural Analysis

Oxime: * 1H NMR 270 MHz JEOL (DMSO): 1.65-1.8 (m, 2H), 2.6-2.8 (m, 4H), 7.1-7.3 (m, 3H), 7.8-7.95 (d, J=7.5 Hz, 1H), 11.1 (s, OH).
* 13C NMR (DMSO): δ 152.5, 137, 132, 129, 128, 126, 123.29, 23, 21.

Oxime acetate: * 1H NMR (CDCl3): 2.75-3.85 (m, 2H), 3.2 (s, 3H), 3.65-3.75 (m, 2H), 3.75-3.85 (m, 2H), 8.05-8.3 (m, 3H), 9.05-9.1 (d, 1H).
* 13C NMR (CDCl3): 169, 162, 141, 131, 128, 127.5, 127, 126, 29, 26, 22, 20.

Enamide: * 1H NMR (CDCl3): 2.1 (s, 3H), 2.25-2.45 (m, 2H), 2.65-2.85 (m, 2H), 6.3 (t, 1H), 7.05-7.35 (m, 4H).
* 13C NMR (CDCl3): 169, 137, 132, 127.5, 127, 126, 121, 120, 28, 24, 22.5.

Example 4

Enamide from 2-Phenylcyclohexanone

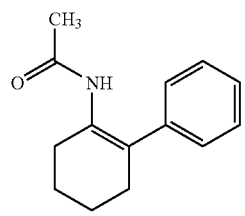

Example 4a

Enamide from 2-Phenylcyclohexanone with Ir/C

Into a 100 ml reactor are introduced tetrahydrofuran (24 ml) and 2-phenylcyclohexanone oxime (4 g, 0.0211 mole). Then acetic anhydride (6.47 g, 0.0634 mole) is added at 20-25° C. over a period of 15 minutes. The suspension is stirred for 1 hour and the catalyst 5% Ir/C (dry catalyst) (0.16 g, 4% by weight relative to oxime) is added. The mixture is heated to 70° C. and the hydrogen flow is started. Hydrogenation is continued over a period of 2.5 to 3 hours under 4 bars hydrogen pressure. After the end of the reaction, the suspension is filtered from the catalyst and the catalyst is washed with THF. This solution is added on a mixture of water (12 ml) and NaOH 30% (10.8 ml) at 5° C. over a period of 1 hour and maintained at 20° C. during 30 minutes. The aqueous phase is discarded and the organic layer is washed with water saturated with NaCl.

The organic layer is concentrated under vacuum at 50° C. to give an oily white residue of N-(2-Phenyl-cyclohex-1-enyl)-acetamide (3.5 g, 77%).

Example 4b

Enamide from 2-Phenylcyclohexanone with Rh/C

Into a 100 ml reactor are introduced tetrahydrofuran (24 ml) and 2-phenylcyclohexanone oxime (4 g, 0.0211 mole). Then acetic anhydride (6.47 g, 0.0634 mole) is added at 20-25° C. over a period of 15 minutes. The suspension is stirred for 1 hour and the catalyst 5% Rh/C (dry catalyst) (0.16 g, 4% by weight relative to oxime) is added. The mixture is heated to 25-30° C. and the hydrogen flow is started. Hydrogenation is continued over a period of 5 to 6 hours under 4 bars hydrogen pressure. After the end of the reaction, the suspension is filtered from the catalyst and the catalyst is washed with THF. This solution is added on a mixture of water (12 ml) and NaOH 30% (10.8 ml) at 5° C. over a period of 1 hour and maintained at 20° C. during 30 minutes. The aqueous phase is discarded and the organic layer is washed with water saturated with NaCl.

The organic layer is concentrated under vacuum at 50° C. to give white crystals of N-(2-Phenyl-cyclohex-1-enyl)-acetamide (3.86 g, 85%).

Structural Analysis

Oxime: 1H NMR (DMSO): 1.4-1.65 (m, 2H), 1.7-1.8 (m, 2H), 1.9-2.2 (m, 3H), 2.8-2.95 (m, 1H), 4.1-4.5 (m, 1H), 7.1-7.4 (m, 5H).

Oxime acetate: * 1H NMR (CDCl3): 1.55-1.75 (m, 4H), 1.85-2.1 (m, 1H), 2.15 (s, 3H), 2.17-2.3 (m, 1H), 2.4-2.5 (m, 1H), 2.75-2.87 (m, 1H), 3.85-3.91 (t, 1H), 7.15-7.4 (m, 5H).

* 13C NMR (CDCl3): 195, 170, 169, 138, 128, 127.5, 126, 46, 31, 27, 25, 22.5, 20.

Enamide: * 1H NMR (CDCl3): 1.65-1.8 (m, 4H), 2.3 (s, 2H), 2.6 (s, 2H), 6.55 (s, NH), 7.1-7.4 (m, 5H).

* 13C NMR (CDCl3): 167, 141, 131, 128, 127.5, 126.5, 126, 31, 27.5, 24, 22.5.

Example 5

Enamide from 2-methoxy-7-tétralone

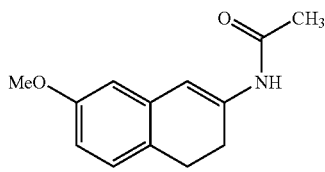

Enamide from 2-methoxy-7-tétralone with Rh/C

Into a 100 ml reactor are introduced tetrahydrofuran (24 ml) and 2-Methoxy-7-tetralone oxime (4.5 g, 0.0235 mole). Then acetic anhydride (7.21 gr, 0.0706 mole) is added at 20-25° C. over a period of 15 minutes. The suspension is stirred for 1 hour and the catalyst 5% Rh/C (dry catalyst)(0.18 gr, 4% by weight relative to oxime) is added. The mixture is heated to 30-35° C. and the hydrogen flow is started. Hydrogenation is continued over a period of 4 to 5 hours under 4 bars hydrogen pressure. After the end of the reaction, the suspension is filtered from the catalyst and the catalyst is washed with THF. This solution is added on a mixture of water (14 ml) and NaOH 30% (12 ml) at 5° C. over a period of 1 hour and maintained at 20° C. during 30 minutes. The aqueous phase is discarded and the organic layer is washed with water saturated with NaCl.

The organic layer is concentrated under vacuum at 50° C. to give grey crystals of N-(7-Methoxy-3,4-dihydro-naphthalen-2-yl)-acetamide (4.21 g, 82.5%).

Structural Analysis

Oxime: 1H NMR (CDCl3): 2.7-2.8 (t, 1H), 2.85-2.95 (t, 1H), 3.45 (s, 2H), 3.75 (s, 3H), 6.65 (m, 2H), 7.1 (m, 1H), 10.05 (s, OH)

Oxime acetate: Non-isolated

Enamide: 1H NMR (CDCl3): 2.1 (s, 3H), 2.35-2.45 (t, 2H), 2.7-2.85 (t, 2H), 3.75 (s, 3H), 6.6 (m, 2H), 6.95 (m, 1H), 7.1 (s, 1H), 7.35 (m, NH)

The invention claimed is:

1. A process for the production of eneamide compounds represented by formula (I)

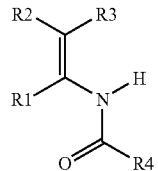

wherein;

R1 and R2 and R3 are independently selected from the group consisting of a hydrogen atom; an alkyl; a cycloalkyl; a cycloalkylalkyl; an alkylaryl; an aryl; a heterocycle; a cyano; an alkoxy; an aryloxy; a carboxyl; a carbamoyl; —CONR5R6 in which R5 and R6 are independently selected from an alkyl, an arylalkyl, an aryl; and R5 and R6 taken together may form a ring; and —COOR5 in which R5 is selected from an alkyl, an alkylaryl, a cycloalkyl, and aryl;

said alkyl, cycloalkyl, cycloalkylalkyl, alkylaryl and aryl being substituted or not substituted with a group selected from a functional group and R5;

R1 and R2 taken together may form a monocyclic ring; a di-cyclic ring and a higher polycyclic ring, said ring being substituted or not substituted with a group selected from a functional group and R5;

R4 is selected from the group consisting of a hydrogen atom, alkyl, aryl and alkylaryl; said alkyl, aryl, and alkylaryl being substituted or not substituted with halogen;

X is selected from an oxygen atom or a leaving group;

m is an integer selected from 1 and 2;

when m is 1X is a leaving group; when m is 2X is an oxygen atom;

said method comprising a hydrogenation/isomerization reaction in presence of a heterogeneous catalyst based on at least one metal selected from Ir and Rh, of an oxime derivative of formula (II)

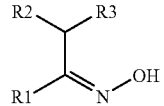

wherein R1, R2 and R3 are as defined above;

with an acyl derivative of formula (III):

(R4CO)$_m$X wherein R4, m and X are is as defined above;

X is selected from an oxygen atom and a leaving group;

m is an integer selected from 1 and 2;

when m is 1 then X is a leaving group; when m is 2 then X is an oxygen atom.

2. The process of claims 1, wherein the derivative of formula (III) is used in the amount selected from at least 2 times per mole based on the oxime, and an amount sufficient to act as a reacting agent and as a solvent.

3. The process of claim 1, wherein the heterogeneous catalyst is in a form selected from a metal oxide and from a metallic form, optionally supported on a suitable carrier; and is used in an amount ranging between 0.001 and 30% mole, based on the oxime derivative.

4. The process of claim 1, which is carried out in a suitable solvent.

5. The process of claim 1, which is carried out under a hydrogen pressure ranging between 0.5 and 20 bars.

6. The process of claim 1, which is carried out under a temperature ranging between −20 and 150° C.

7. The process of claim 1, further comprising a work up step of an organic solution of the compound of formula (I) which is a washing step with water containing organic or mineral salt(s) without halogen atom.

8. The process of claim 7, wherein the organic or mineral salt(s) is/are selected from the group consisting of phosphate, sulfate, acetate, citrate, formate, borate, carbonate, or ammonium.

9. The process of claim 1, wherein said eneamide is selected from the group consisting of:
N-(6-Methoxy-3H-inden-1-yl)-acetamide;
N(3,4-dihydro-1-naphtalenyl)acetamide;
N(3,4-dihydro-naphtalen-2-yl)acetamide;
N-(2-Phenyl-cyclohex-1-enyl)-acetamide; and
N-(7-Methoxy-3,4-dihydro-naphthalen-2-yl)-acetamide.

10. A method of manufacture of an amine or an amide compound comprising:
performing a hydrogenation reaction of a eneamide compound selected from:
a) an ene-amide of formula (IIE)

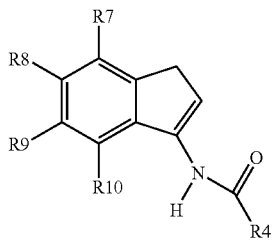

(IIE)
wherein R4 is selected from the group consisting of hydrogen, alkyl, aryl and alkylaryl; said alkyl, aryl, and alkylaryl being substituted or not substituted with halogen;
R7, R8, R9 and R10 are independently selected from the group consisting of hydrogen; functional group, halogen; a group comprising —OH, —ORS, —CN, —COOR5, —COR5, —CONR5R6, —OCOR5, —NH2, —NHR5, —NR5R6, —NO2, —SH and —SR5, wherein R5 and R6 are independently an alkyl, an alkylaryl or an aryl group or R5 and R6 taken together may form a ring; alkyl and aryl, while not simultaneously being hydrogen;
b) N(3,4-dihydro-1-naphtalenyl)acetamide;
c) N(3,4-dihydro-naphtalen-2-yl)acetamide;
d) N-(2-Phenyl-cyclohex-1-enyl)-acetamide; and
e) N-(7-Methoxy-3,4-dihydro-naphthalen-2-yl)-acetamide;
to obtain a hydrogenated compound;
said method comprising, prior to said hydrogenation reaction of said eneamide, preparing said eneamide by performing a hydrogenation/isomerisation reaction of the corresponding oxime in the presence of a heterogeneous catalyst based on at least one metal selected from Ir and Rh, with an acyl derivative of formula (III) $(R_4CO)_mX$, to obtain a hydrogenated compound of formula I, by the method as defined in claim 1 wherein R1 and R2 taken together form a di-cyclic ring.

11. The method of claim 10, wherein said hydrogenation reaction performs an asymmetric hydrogenation of said compound of formula (IIE), thereby obtaining a chiral amide or amine.

12. The method of claim 10, wherein the eneamide compound is selected from the group consisting of:
N-(6-Methoxy-3H-inden-1-yl)-acetamide;
N(3,4-dihydro-1-naphtalenyl)acetamide;
N(3,4-dihydro-naphtalen-2-yl)acetamide;
N-(2-Phenyl-cyclohex-1-enyl)-acetamide; and
N-(7-Methoxy-3,4-dihydro-naphthalen-2-yl)-acetamide.

13. A process for production of eneamide compounds represented by formula (I)

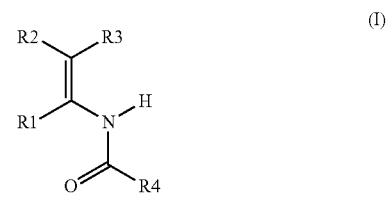

wherein;
R1 and R2 and R3 are independently selected from the group consisting of a hydrogen atom; an alkyl; a cycloalkyl; a cycloalkylalkyl; an alkylaryl; an aryl; a heterocycle; a cyano; an alkoxy; an aryloxy; a carboxyl; a carbamoyl; —CONR5R6 in which R5 and R6 are independently selected from an alkyl, an arylalkyl, an aryl; and R5 and R6 taken together may form a ring; and —COOR5 in which R5 is selected from an alkyl, an alkylaryl, a cycloalkyl, and aryl;
said alkyl, cycloalkyl, cycloalkylalkyl, alkylaryl and aryl being substituted or not substituted with a group selected from a functional group and R5;
R1 and R2 taken together may form a monocyclic ring; a di-cyclic ring and a higher polycyclic ring, said ring being substituted or not substituted with a group selected from a functional group and R5;
R4 is selected from the group consisting of a hydrogen atom, alkyl, aryl and alkylaryl; said alkyl, aryl, and alkylaryl being substituted or not substituted with halogen;
said method comprising a hydrogenation/isomerization reaction in presence of a heterogeneous catalyst based on at least one metal selected from Ir and Rh, of an oxime derivative of formula (II)

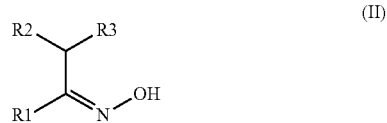

wherein R1, R2 and R3 are as defined above;
with an acyl derivative of formula (III):

$(R4CO)_mX$ wherein R4 is as defined above;
X is selected from an oxygen atom and a leaving group;
m is an integer selected from 1 and 2;
when m is 1 then X is a leaving group; when m is 2 then X is an oxygen atom;
wherein the heterogeneous catalyst is in a form selected from a metal oxide and from a metallic form, optionally supported on a suitable carrier; and is used in an amount ranging between 0.001 and 30% mole, based on the oxime derivative.

14. A method of manufacture of an amine or an amide compound comprising (i) performing a hydrogenation/isomerization reaction of

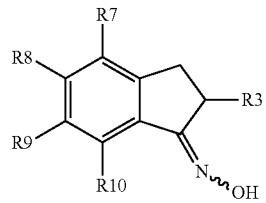

with an acyl derivative of formula (III) $(R_4CO)_mX$, in the presence of a heterogeneous catalyst based on at least one metal selected from Ir and Rh, to form the ene-amide compound of formula (IIE)

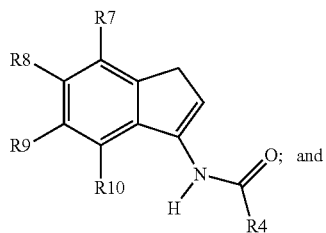

(ii) hydrogenating the compound of formula (IIE) to form a chiral amine or a chiral amide, R4 is selected from the group consisting of hydrogen, alkyl, aryl, and alkylaryl being substituted or not substituted with halogen; R7, R8, R9 and R10 are independently selected from the group consisting of hydrogen; halogen; a group comprising —OH, —ORS, —CN, —COOR5, —COR5, —CONR5R6, —OCOR5, —NH2, —NHR5, —NR5R6, —NO2, —SH and —SR5, wherein R5 and R6 are independently an alkyl, an alkylaryl or an aryl group or R5 and R6 taken together may form a ring; alkyl and aryl, while not simultaneously being hydrogen.

15. The process of claim 14, wherein the heterogeneous catalyst is in a form selected from a metal oxide and from a metallic form, optionally supported on a suitable carrier; and is used in an amount ranging between 0.001 and 30% mole, based on the oxime derivative.

* * * * *

UNITED STATES PATENT AND TRADEMARK OFFICE
CERTIFICATE OF CORRECTION

PATENT NO.          : 7,884,243 B2                              Page 1 of 1
APPLICATION NO.     : 10/583902
DATED               : February 8, 2011
INVENTOR(S)         : Burgos et al.

It is certified that error appears in the above-identified patent and that said Letters Patent is hereby corrected as shown below:

Col. 16, line 10, claim 14: "comprising -OH, -ORS, -CN," should read --comprising -OH, -OR5, -CN,--

Signed and Sealed this
Twenty-first Day of June, 2011

David J. Kappos
*Director of the United States Patent and Trademark Office*